United States Patent [19]

Ashkar

[11] 4,067,718
[45] Jan. 10, 1978

[54] METHOD FOR CONTROLLING THE RELATIVE STEM GROWTH OF PLANTS

[75] Inventor: Saleh Abdul-Kadir Ashkar, Lawrenceville, N.J.

[73] Assignee: American Cyanamid Company, Stamford, Conn.

[21] Appl. No.: 631,359

[22] Filed: Nov. 12, 1975

[51] Int. Cl.$^2$ .............................................. A01N 9/22
[52] U.S. Cl. ......................................... 71/76; 71/92; 71/78
[58] Field of Search ..................................... 71/76, 92

[56] References Cited

U.S. PATENT DOCUMENTS 3,409,425  11/1968  Bousquet et al. ........................ 71/76
3,849,436  11/1974  Johnson ............................... 71/92 X Primary Examiner—Lewis Gotts
Assistant Examiner—Catherine L. Mills
Attorney, Agent, or Firm—Bruce F. Jacobs

[57] ABSTRACT

The invention relates to a method for controlling the relative stem growth of plants by applying to the foliage of the plants, or to soil containing seeds of the plants, a plant-growth-regulating amount of an imidazoisoindoledione or dihydroimidazoisoindoledione or an optical or stereo isomer thereof.

18 Claims, No Drawings

METHOD FOR CONTROLLING THE RELATIVE STEM GROWTH OF PLANTS

BACKGROUND OF THE INVENTION

1. Field of the Invention

The invention pertains to the use of imidazoisoindolediones and dihydroimidazoisoindolediones as plant growth regulants.

2. Description of the Prior Art

The compounds useful in this invention are disclosed in Marinus Los' copending U.S. application Ser. Nos. 631,356 and 631,357, filed Nov. 12, 1975 and Nov. 12, 1975, respectively, the latter now U.S. Pat. No. 4,017,510 Intermediates used in the manufacture of the compounds useful in the invention are disclosed in Netherlands Pat. No. 7,311,503, published Feb. 25, 1974 and assigned to the American Cyanamid Company. The corresponding U.S. application is copending Ser. No. 382,418 filed July 25, 1973 now U.S. Pat. No. 3,940,419.

SUMMARY OF THE INVENTION

The invention relates to a method for controlling plant growth by applying to the foliage thereof or to soil containing seeds of the plant, a plant-growth-regulating amount of a compound of the formula:

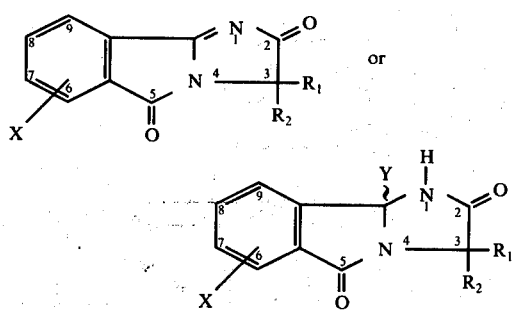

wherein X is H, $CH_3NO_2$, Cl, $OCH_3$ or $SCH_3$; $R_1$ and $R_2$ each represent alkyl $C_1$-$C_4$, providing that the sum of the carbon atoms in the groups represented by $R_1$ and $R_2$ is 4 to 7, and when $R_1$ and $R_2$ are taken together with the carbon to which they are attached, they may form cycloalkyl $C_5$-$C_6$ optionally substituted with methyl; Y represents hydrogen; and the optical and stereoisomers thereof.

DESCRIPTION OF THE PREFERRED EMBODIMENTS

Preferred compounds for use as plant growth regulators are represented by formulas I and II above, wherein X is H, Cl, $CH_3$ or $-SCH_3$; Y is hydrogen; and $R_1$ and $R_2$ are alkyl $C_1$-$C_4$ provided that the sum of the carbon atoms represented thereby is 4 or 5, or when $R_1$ and $R_2$ are taken together with the carbon to which they are attached they represent cycloalkyl $C_5$-$C_6$.

The compounds of the present invention are highly effective plant growth regulating agents. They may be used effectively for controlling the relative stem growth of both monocotyledonous and dicotyledonous plants by application thereof to the foliage of the plants, or by application to soil containing seeds of the plants. Generally, one treatment is effective on the total growth of the plant; however, repeated treatments are frequently found to increase the extent of the effect. The most characteristic growth alterations brought about by the treatment (using formula I or II compounds where X is a substituent other than chloro) are shorter, thicker stems, reduction in tillering and reduction is sucker growth. As such, the compounds of this invention (as defined above) are found to be particularly useful for treating roadside plantings, where it is desirable to reduce the number of grass cuttings and shrub prunings needed for proper grooming during the growing season. These compounds are also useful for dwarfing cereal grains such as rice, barley and wheat, and preventing lodging thereof. Usually, about 0.25 to 4.0 pounds per acre or 0.25 to 4.48 kg/hectare, and preferably 1.12 to 4.48 kg/hectare of the active compound is effective for achieving this dwarfing effect for compounds wherein $R_1$ and $R_2$ represent $C_5$-$C_6$ cycloalkyl or 0.28 to 1.2 kg/hectare where $R_1$ and $R_2$ are alkyl and have a total of 4 to 5 carbon atoms.

Surprisingly, I have also found that certain of the compounds of this invention, particularly those of formula I, wherein X is Cl and $R_1$ and $R_2$ each represent alkyl $C_1$-$C_4$, provided that the sum of the carbon atoms represented by $R_1$ and $R_2$ is 5 to 7, or when $R_1$ and $R_2$, taken together with the carbon to which they are attached, represent cycloalkyl $C_5$-$C_6$; induce a pronounced increase in relative stem length and/or foilage weight of plants, particularly dicotyledonous plants, when applied at rates of from about 0.25 to 10 pounds per acre or from 0.28 to 11.2 kg/hectare, either to the foilage of plants or to soil containing seeds thereof. These compounds thus find utility as growth enhancing agents for crops, particularly broadleaf crops such as soybeans, cotton, cucumbers and snapbeans. It is, however, also found that these compounds are useful for enhancing the growth rate of sorghum and corn.

The plant growth regulating effects of the compounds of the present invention are further demonstrated by the compounds' usefulness for controlling sucker growth on mechanically topped tobacco plants. With the compounds of this invention, it is found that solutions and/or suspensions, preferably aqueous, containing from about 200 to 2000 ppm, and preferably 200 to 1000 ppm, or active compound is effective for inhibiting sucker growth on mechanically topped tobacco plants.

In tobacco farming, bud growth is conventionally controlled by two mechanical processing operations. Plant height is regulated by cutting off the terminal bud flower of the tobacco plant in a process known as "topping." This process facilitates the development of the large leaf which forms the commercial crop. Their development is, however, offset by the enhanced development of lateral (axillary) buds. The lateral growth (called "sucker growth") again reduces the nutrient supply available for large leaf development. This necessitates a second mechanical operation; namely, the hand removal of the suckers from each tobacco plant. In the practice of the present invention, the inconvenient and expensive mechanical steps can be avoided by two spraying operations. Firstly, terminal bud development can be controlled by an over-spraying of the active ingredient. Secondly, sucker development can be controlled by a subsequent spraying of the plant stem and foliage.

Harvesting of the marketable or prime leaves of flue-cured tobacco is usually begun about 1 or 2 weeks after treatment and may continue for 4 or 5 weeks. Usually the leaves are cut from the bottom of the stalk in groups of three at weekly intervals. Inhibiting growth of axillary buds during this period is important since such treatment results in improved quality, texture, and yield of the prime or marketable leaves. Inhibiting growth of axillary buds on topped burley tobacco is also important from the standpoint of improving quality and yield of tobacco, although the harvesting procedure is somewhat different. Accordingly, after the burley tobacco is topped, it is sprayed with a solution of the active material to inhibit axillary bud development, and the whole stalk is then harvested in accordance with standard practices some five to ten weeks after treatment.

Inasmuch as the compounds of this invention are only very slightly water soluble, they are generally formulated for foilar treatments as wettable powders or flowable liquids which are usually dispersed in water or other inexpensive liquid diluent for application to said foliage as a liquid spray. However, when said compounds are to be used where soil treatments are involved, the compounds of the invention may also be prepared as granular products.

A typical wettable powder can be prepared by grinding together approximately 46% by weight of a finely divided carrier such as attapulgite, 50% by weight of the imidazoisoindoledione or dihydroimidazoisoindoledione of this invention, 3% by weight of the sodium salt of condensed naphthalene sulfonic acids and 1% by weight of sodium N-methyl-N-oleoyltaurate.

A typical flowable liquid can be prepared by admixing about 42% by weight of the imidazoisoindoledione or dihydroimidazoisoindoledione, with about 3% by weight of the sodium salt of condensed naphthalene sulfonic acids, 2% by weight of finely divided bentonite and 53% by weight of water.

A granular product can be prepared by dissolving the imidazoisoindoledione or dihydroimidazoisoindoledione in methylene chloride and spraying the thus-prepared solution on a granular carrier such as sand, silica, kaolin, corn cob grits, attapulgite, or the like.

In accordance with this invention, formula I imidazoisoindoledione can be prepared by cyclization of a phthalimidocarboxamide or a dioxoisoindolineacetamide. Cyclization can be achieved by reacting the said phthalimido derivative or isoindolineacetamide with a strong base, at an elevated temperature in the presence of an organic solvent.

The cyclization reaction is preferably conducted at a temperature of from 80° C to 150° C in the presence of a base such as sodium or potassium hydroxide, or an acid catalyst such as an aromatic sulfonic acid and a solvent which will azeotrope with water, permitting virtually immediate removal thereof from the reaction mixture as it is formed.

Among the solvents which may be employed are toluene, benzene, xylenes and cyclohexane.

Bases which may be used include alkali metal hydroxides, alkali metal hydrides, alkali metal oxides, tertiary amines such as diisopropyl ethylamine, 1,5-diazobicyclo[3.4.0]-nonene-5; 1,5-diazobicyclo[5.4.0]undecane-5; 1,4-diazobicyclo[2.2.2]octane; tetramethylguanidine, potassium fluoride and quaternary ammonium hydroxides such as trimethylbenzyl ammonium hydroxide and strongly basic ion exchange resins.

Acidic reagents which may be employed include aromatic sulfonic acid such as p-toluenesulfonic acid, β-naphthalenesulfonic acid, naphthalenedisulfonic acid, and the like.

In many cases, the ring closure may also be achieved by a simple pyrolysis of the phthalimidocarboxamide or dioxoisoindolineacetamide at a temperature between 80° C and 250° C.

These reactions may be illustrated as follows:

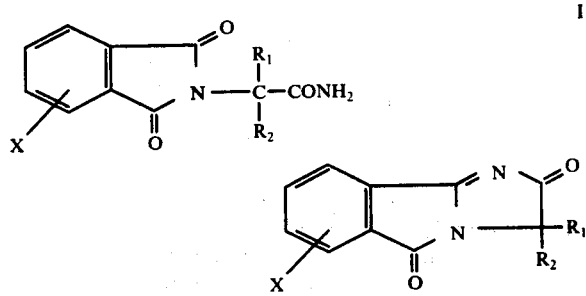

It should also be understood that, in the above reaction, when X is not hydrogen the product of the reaction is a mixture of the two isomeric compounds since cyclization occurs at either imide carbonyl group as illustrated below:

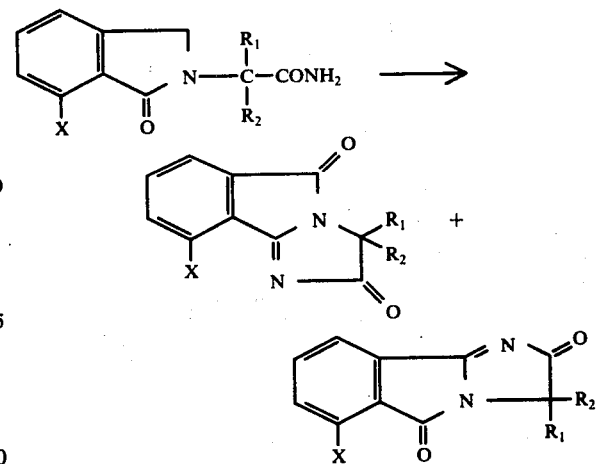

Furthermore, when $R_1$ and $R_2$ represent different groups, the carbon to which $R_1$ and $R_2$ are attached is an asymmetric center and the products (as well as their intermediates) exist in d- and l- forms.

Formula I imidazoisoindolediones can also be prepared by cyclization of the appropriate alkyl N-(carbamoylalkyl) phthalamate with an alkali metal hydride such as sodium or potassium hydride, in the presence of an inert organic solvent such as toluene, xylene or benzene at an elevated temperature of about 80° C to 150° C. This reaction may be illustrated, using NaH as representative of the alkali metal hydride, as follows:

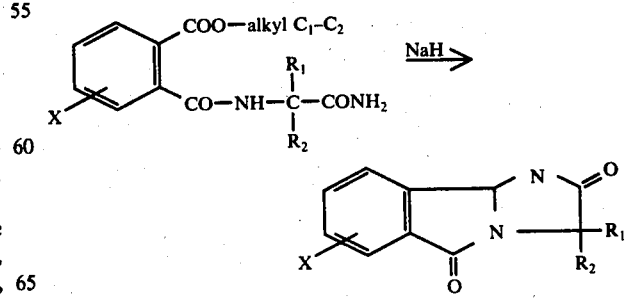

wherein X, $R_1$ and $R_2$ are as described above. This reaction is especially useful for the preparation of imidazoisoindolediones in which $R_1$ and $R_2$ represent bulky groups such as isopropyl or t-butyl groups.

Furthermore, as with the previously described method for the preparation of the formula I imidazoisoindolediones, when $R_1$ and $R_2$ represent different groups, carbon atom to which they are attached is an asymmetric carbon atom. Therefore, if one starts with an optically active intermediate such as α-aminocarbonitrile, α-aminocarboxylic acid or α-aminocarboxamide, the intermediate N-(carbamoylalkyl) phthalamate and the imidazoisoindoledione, thus prepared, are optically active.

Conversion of the imidazoisoindoledione (I) to the dihydroimidazoisoindoledione (II) is achieved by a reduction reaction. This reaction may be carried out with sodium borohydride or a catalyst such as platinum or palladium catalyst, preferably on a carbon, silica or alumina support. The catalytic reduction is generally conducted under superatmospheric pressure between about 10 psig and 150 psig at an elevated temperature between 80° C and 150° C.

When $R_1$ and $R_2$ represent different groups on the formula II dihydroimidazoisoindolediones, cis and trans isomers (stereoisomers) are obtained and both isomers are found to be biologically active.

This reaction may be graphically illustrated as follows:

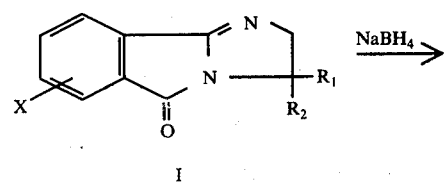

I

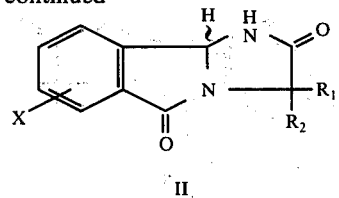

II

The intermediate phthalimidocarboxamide or dioxoisoindolineacetamide, which is essential to the preparation of the formula I imidazoisoindolediones of the present invention, can be prepared by reacting an appropriate disubstituted ketone with ammonium chloride, sodium cyanide and ammonium hydroxide, to obtain the α,α-disubstituted-α-aminocarbonitrile. This α-aminonitrile is then reacted with phthalic anhydride to give the corresponding phthalamic acid.

This reaction is carried out at temperatures from about 20° C to 60° C in an inert solvent such as ether, tetrahydrofuran, chloroform, methylene chloride, benzene, toluene and the like. The thus-formed phthalamic acid is then cyclized to the corresponding phthalimidocarbonitrile by heating with a dehydrating agent such as acetic anhydride, acetyl chloride, thionyl chloride, or the like, at temperatures from about 0° C to 100° C. Hydration of the thus-formed phthalimidocarbonitrile is preferably carried out with a strong acid such as sulfuric acid, with or without the addition of a non-miscible solvent such as methylene chloride or chloroform and the like at temperatures from about −10° C to +30° C. These reactions are graphically illustrated by using the substituted phthalic anhydride as an example, and including the cyclization of the phthalimidocarboxamide to form the compounds of this invention, as follows:

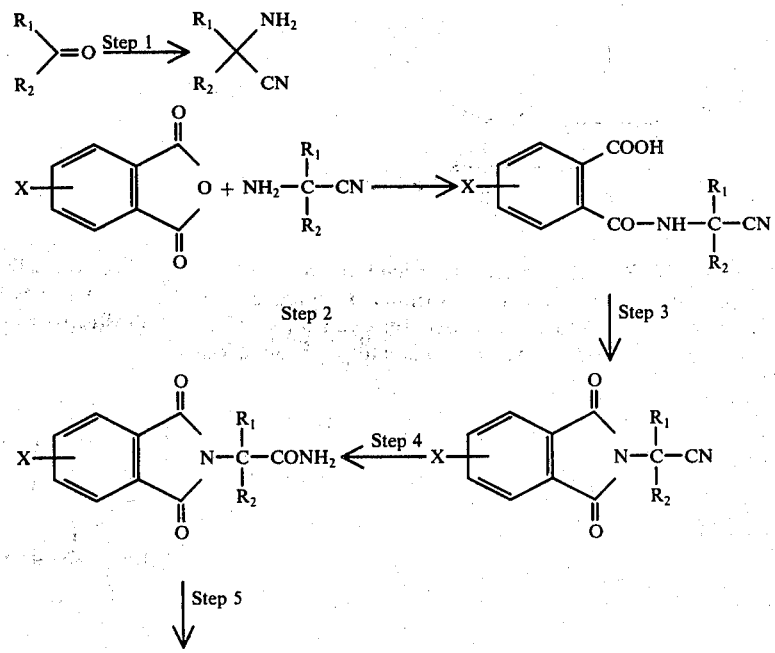

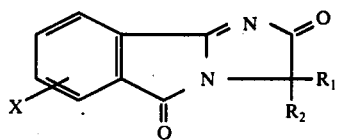

(I)

wherein X, $R_1$ and $R_2$ are as described above.

Alternatively, the above-mentioned intermediate phthalimidocarboxamide may also be prepared by the reaction of phthalic anhydride with a substituted aminocarboxylic acid to obtain the phthalimidocarboxylic acid which is converted to the corresponding acid chloride using thionyl chloride. This reaction is generally conducted in the presence of an inert organic solvent such as toluene, benzene, or the like, at an elevated temperature. The acid chloride is then readily converted to the intermediate phthalimidocarboxamide by reaction with ammonia. This reaction is generally conducted in the presence of a solvent such as tetrahydrofuran at a temperature between about $-10°$ C and $+15°$ C. This synthetic route, including the cyclization of the phthalimido carboxamide, is illustrated as follows:

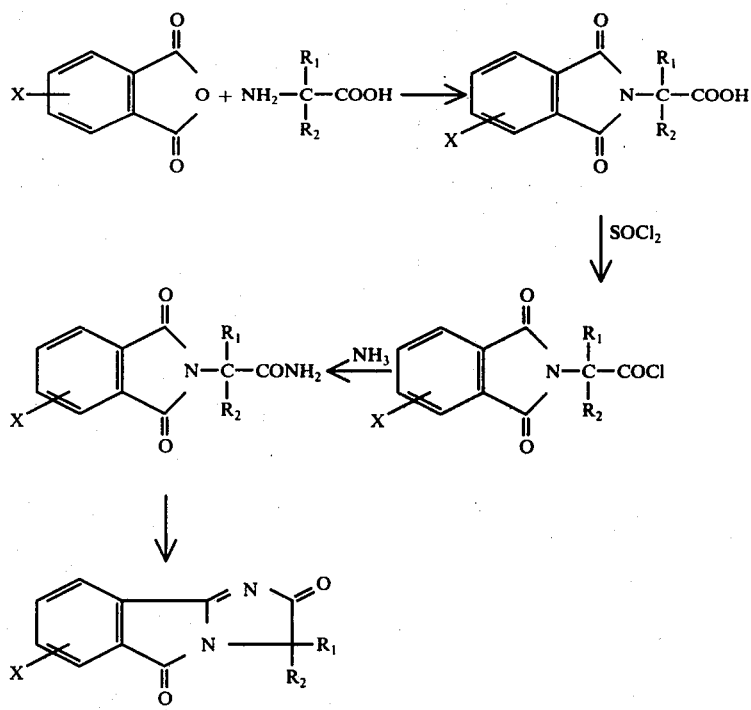

wherein X, $R_1$ and $R_2$ are as described above.

As previously indicated, formula I imidazoisoindolediones can also be prepared by cyclization of an alkyl N-(carbamoylalkyl) phthalamate with an alkali metal hydride. The intermediate α-aminocarboxamide required for the preparation of the alkyl N-(carbamoylalkyl) phthalamate, which is represented by the formula:

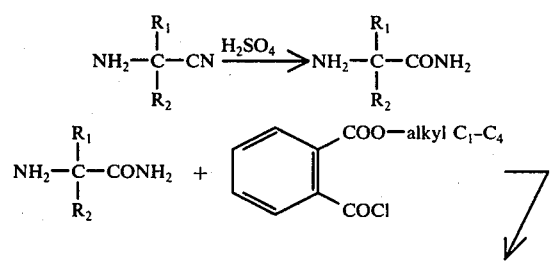

where $R_1$ and $R_2$ are as previously described, can be prepared by reacting an α-aminocarbonitrile with sulfuric acid at an elevated temperature. This carboxamide is then reacted with a 2-carboalkoxybenzoyl chloride to yield the alkyl N-(carbamoylalkyl) phthalamate, referred to above. These reactions may be graphically illustrated as follows:

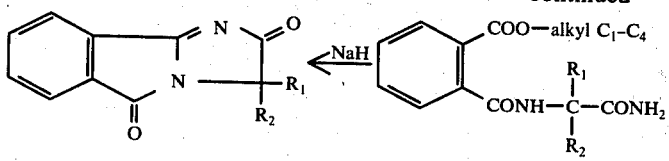

This invention is further demonstrated by the examples set forth below.

EXAMPLE 1

Preparation of 3-Isobutyl-3-methyl-5H-imidazo[2,1-a]-isoindole-2(3H),5-dione.

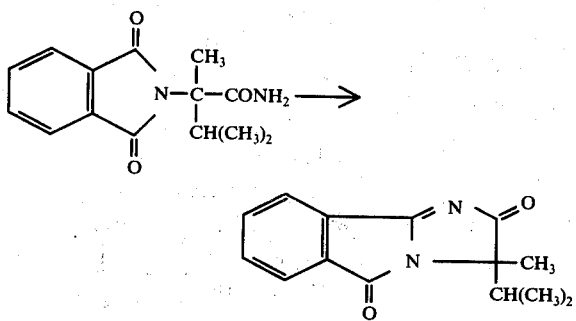

A solution of 130.1 g (0.5 mole) of α-isopropyl-α-methyl-1,3-dioxo-2-isoindolineacetamide in 650 ml toluene is heated with vigorous stirring under a Dean-Stark water separator in order to remove traces of water. The solution was cooled to 100° C and 2.0 g sodium hydroxide in the form of pels is added and the mixture rapidly heated to reflux. Water collects in the water separator. One-half hour after the addition of the sodium hydroxide, a further 2 g is added and heating is continued for a further 1¼ hours when no further water is removed from the reaction mixture and the infrared spectrum of an aliquot indicates the reaction to be complete. The reaction mixture is cooled to room temperature, filtered and the solids washed with toluene and the toluene removed in vacuo to leave a white solid which is transferred to a filter funnel with hexane and air-dried to give 98.7 g. of 2,5-dihydro-3-isopropyl-3-methyl-3H-imidazo[2,1-a]isoindole-2,5-dione, melting point 93°–96° C. The product may be purified by recrystallization from hexane to give an analytically pure sample, melting point 98°–100.5° C.

Alternatively, the product may be isolated by adding a slight excess of glacial acetic acid over the amount of sodium hydroxide used to the toluene reaction mixture, adding water, separating the organic phase, washing the organic phase with water, separating the organic phase, drying the organic phase, and finally removing the solvent to yield the product.

The above procedure is repeated in all respects, excepting that the strong base reagent is altered. In separate experiments, sodium hydride, potassium hydroxide, barium oxide, diisopropylethylamine, 1,5-diazobicyclo[5.4.0]undicene-5, tetramethylguanidine, tetramethylbenzyl ammonium hydroxide, Amberlite A21 (Rohm & Haas) strongly basic ion exchange resin and p-toluenesulfonic acid, are substituted for sodium hydroxide and yield the desired 3-isopropyl-3-methyl-5H-imidazo[2,1-a]isoindole-2(3H),5-dione. In practice of the above-described method, sodium hydroxide or sodium hydride in refluxing toluene is preferred.

Using the procedure described above, but substituting the appropriate phthalimidocarboxamide or dioxoisoindolineacetamide for α-isopropyl-α-methyl-1,3-dioxo-2-isoindolineacetamide, and the selected strong base and solvent for sodium hydroxide and toluene, yields the imidazoisoindolinediones reported in Table I below. Table I also indicates the solvent and base used as well as the melting point of the compounds obtained. With regard to the compounds synthesized and reported in Table I, it should be understood that when Y≠H the product is a mixture of two isomeric compounds, since cyclization occurs at both imidecarbonyl groups, for example:

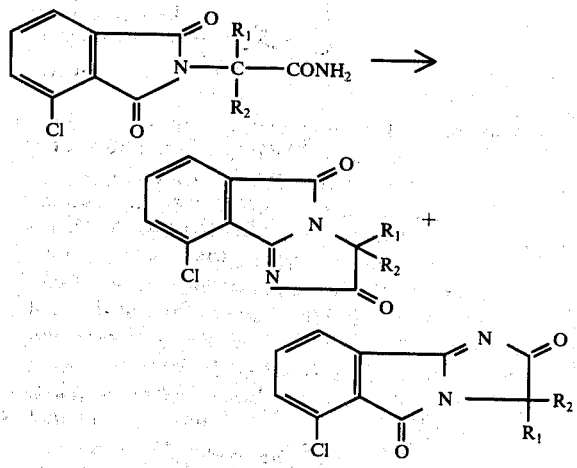

In some cases, as shown in Table I, there are separated either by fractional crystallization or column chromatography. In the other cases, the mixture, indicated by a two-number prefix before the substituent X is tested for biological activity.

TABLE I

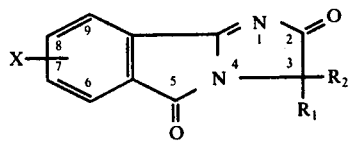

| Catalyst or Base | Solvent | X | R₁ | R₂ | Melting Point °C |
|---|---|---|---|---|---|
| NaH | Toluene | H | —CH—CH₂—CH₂—CH₂—CH₂—<br>\|<br>CH₃ | | 133.5–135 |
| NaH | Toluene | 9-Cl | | (CH₂)₅ | 251–252 |
| NaH | Toluene | 6-Cl | | (CH₂)₅ | 156.5–157.5 |
| NaH | Toluene | H | —CH₃ | —CH(C₂H₅)₂ | 99–101 |
| NaH | Toluene | H | —CH₃ | —CH(CH₃)(C₂H₅) | 85.5–87.5 |
| NaH | Toluene | 7/8-CH₃ | | (CH₂)₅ | 183–187 |
| NaH | Toluene | H | | (CH₂)₅ | 158–162 |
| NaH | Toluene | 6/9-SCH₃ | | (CH₂)₅ | 263.5–264 |
| NaH | Toluene | 6-Cl | —CH₃ | —CH₂CH(CH₃)₂ | 122–124 |
| NaH | Toluene | 9-Cl | —CH₃ | —CH₂CH(CH₃)₂ | 152–154 |
| NaH | Toluene | H | —CH₃ | —CH₂CH(CH₃)₂ | 98.5–99 |

EXAMPLE 2

Preparation of 3-tert-Butyl-3-methyl-5H-imidazo[2,1-a]-isoindole-2(3H),5-dione.

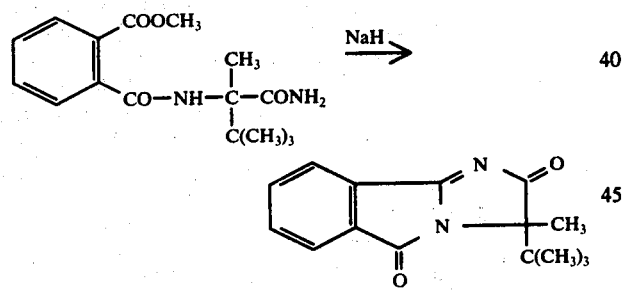

A suspension of sodium hydride (from 1.92 g of a 50% suspension of sodium hydride in mineral oil) in 150 ml toluene is heated under reflux. During 20 minutes is then added portionwise 6.13 g (0.02 mole) methyl N-(1-carbamoyl-1,2,2-trimethylpropyl)phthalamate to the stirred, refluxing, mixture. Heating is continued for 30 minutes after the addition, the mixture filtered through diatomaceous earth, and the solvent removed in vacuo. The residue crystallizes and is recrystallized from a mixture of acetone-hexane to give 3-t-butyl-3-methyl-5H-imidazo[2,1-a]isoindole-2(3H),5-dione, melting point 136.5°–137.5° C.

The 3,3-diisopropyl-5H-imidazo[2,1-a]isoindole-2(3H),5-dione (melting point 146°–148° C) is prepared in the manner described above, excepting that the methyl ester of N-(1-carbamoyl-1-isopropyl-2-methyl-propyl)phthalamic acid is substituted for methyl N-(1-carbamoyl-1,2,2-trimethylpropyl)phthalamate, in the above reaction.

EXAMPLE 3

Preparation of 1,9b-Dihydro-3-isobutyl-3-methyl-5H-imidazo[2,1-a]isoindole-1(3H),5-dione.

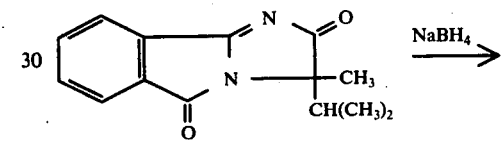

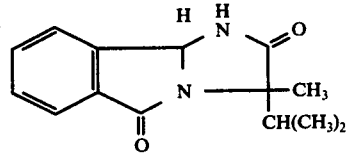

To a stirred suspension of 10.4 g (0.274 mole) sodium borohydride in 164 ml absolute ethanol under nitrogen was added dropwise at 5° C a solution of 133.9 g (0.548 mole) of 2,5-dihydro-3-isopropyl-3l-methyl-3H-imidazo[2,1-a]isoindole-2,5-dione in 155 ml tetrahydrofuran. After the addition, the mixture is stirred a further 3 hours at room temperature and then poured over 1070 g ice with stirring. The mixture is acidified with concentrated HCl and after stirring for 1.5 hours, the precipitate removed by filtration, washed with water and air-dried to give 118.7 g of 1,9b-dihydro-3-isopropyl-3-methyl-5H-imidazo[2,1-a]isoindole-2(3H),5-dione, melting point 178°–200° C.

This compound is a mixture of stereoisomers which can be graphically represented as follows:

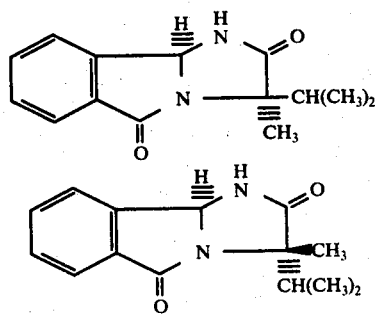

These isomers may be separated by fractional crystallization from acetonitrile to give the less soluble isomer, melting point 234°–236° C and the more soluble isomer, melting point 217°–221° C, which are readily distinguishable by their nmr spectra. It is also understood that each of these stereoismers exists as a pair of optical isomers by virtue of the asymmetric carbon atom bearing the methyl and isopropyl groups.

The reduction can be carried out in lower alkyl alcohols with or without the addition of water at temperatures preferably between 0° C to 25° C. Other reducing agents such as sodium cyanoborohydride and lithium borohydride may be used to effect this transformation.

The following compounds listed in Table II below are prepared essentially by the procedure described above, but substituting the appropriate imidazoisoindoledione for 3-isopropyl-3-methyl-5H-imidazo[2,1-a]isoindole-2-(3H),5-dione, in said procedure. The broad melting points shown in Table II reflect the fact that the compounds are mixtures of cis and trans isomers when $R \neq R_2$ and that each steroisomer is a mixture of positional isomers with respect to X when $X \neq H$.

TABLE II

| X | $R_1$ | $R_2$ | Melting Point °C |
|---|---|---|---|
| H | —CH—CH$_2$—CH$_2$—CH$_2$—CH$_2$— with CH$_3$ branch | | 252–261 |
| 7/8-CH$_3$ | | (CH$_2$)$_5$ | 195–203 |
| H | —CH$_3$ | —CH(C$_2$H$_5$)$_2$ | 179–185 |
| H | —CH$_3$ | —CH(CH$_3$)(C$_2$H$_5$) | 160–190 |
| H | | (CH$_2$)$_4$ | 230–232 |
| 9-Cl | | (CH$_2$)$_5$ | 200–201 |
| 6-Cl | | (CH$_2$)$_5$ | |
| H | | (CH$_2$)$_5$ | 238–239.5 |
| 6/9-SCH$_3$ | | (CH$_2$)$_5$ | 175–185 |
| Cl | —CH$_3$ | —CH$_2$CH(CH$_3$)$_2$ | 145–195 |
| H | —CH$_3$ | —CH$_2$CH(CH$_3$)$_2$ | 190–209 |

EXAMPLE 4

Four-Step Synthesis for the Preparation of Phthalimidocarboxamide Derivatives Essential for the Preparation of Formula I, Imidazoisoindolediones.

Step 1. Preparation of the α-Aminonitrile

To a mixture containing 70 g (1.477 mole) ammonium chloride and 61.36 g (1.25 mole) sodium cyanide in 400 ml 28% ammonium hydroxide solution is added dropwise with stirring and cooling 86.1 g (1 mole) diethylketone. After stirring overnight, the organic phase is separated and the aqueous phase extracted twice with methylene chloride. The organic phase and extracts are combined, washed with water and dried. The drying agent is removed and the solvent removed in vacuo to leave essentially pure 2-amino-2-ethylbutyronitrile, as shown by the absence of a carbonyl band (1700–1720 cm$^{-1}$) in the infrared spectrum. The aminonitriles can be purified if contaminated with starting ketone by dissolving the crude product in ether, adding anhydrous hydrogen chloride and collecting the precipitated hydrochloride salt. The free aminonitrile can then be regenerated by distributing the salt between methylene chloride and aqueous sodium bicarbonate solution, washing the organic phase with water, drying the organic phase and finally removing the solvent in vacuo.

Using this procedure, the following aminonitriles, reported in Table III below, are prepared as oils and characterized only by their infrared spectra.

TABLE III

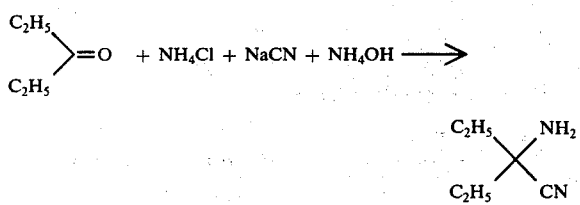

| R | $R_1$ |
|---|---|
| —CH—CH$_2$—CH$_2$—CH$_2$—CH$_2$— with CH$_3$ branch | |
| —CH$_3$ | —C(CH$_3$)$_3$ |
| —CH$_3$ | —CH(CH$_3$) (C$_2$H$_5$) |
| —C$_2$H$_5$ | —C$_2$H$_5$ |
| —CH(CH$_3$)$_2$ | —CH(CH$_3$)$_2$ |
| (CH$_2$)$_5$ | |
| (CH$_2$)$_4$ | |

Step 2. Preparation of the Phthalamic Acids.

The following is a typical procedure:

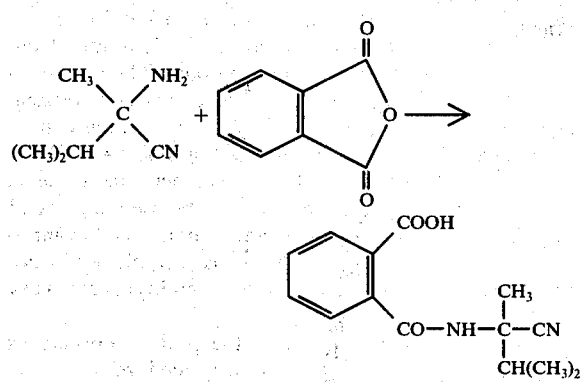

To a stirred boiling mixture of 28.1 g (0.189 mole) of phthalic anhydride in 28 ml methylene chloride is added dropwise 23.6 g (0.21 mole) of 2-amino-2,3-dimethylbutyronitrile in 57 ml methylene chloride. After the addition, heating is continued for 3 hours. The mixture is cooled and the precipitate removed by filtration, washed with methylene chloride and air-dried to give 44.2 g (90%) of N-(1-cyano-1,2-dimethylpropyl)phthalamic acid, melting point 154°–155° C.

Other solvents such as ether, tetrahydrofuran, chloroform, benzene and toluene may be used in place of methylene chloride. The reaction can be run at temperatures from 0°–100° C, but preferably at 20°–50° C.

The phthalamic acids of Table IV are prepared by the general method described above using the appropriate phthalic anhydride and appropriate aminonitrile.

TABLE IV

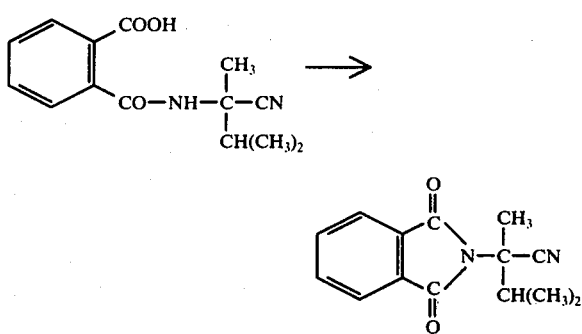

| $R_1$ | $R_2$ | X | Melting Point °C |
|---|---|---|---|
| —CH—CH$_2$—CH$_2$—CH$_2$—CH$_2$—<br>\|<br>CH$_3$ | | H | 158 – 162 |
| —CH$_3$ | —CH(C$_2$H$_5$) (CH$_3$) | H | 153.5 – 154.5 |
| —CH$_3$ | —CH(C$_2$H$_5$)$_2$ | H | 109 – 113 |

Step 3. Preparation of the Phthalamide Nitriles.

The following is a typical procedure:

A suspension of 26 g (0.1 mole) of N-(1-cyano-1,2-dimethylpropyl)phthalamic acid in 130 ml methylene chloride is heated with stirring under reflux. Thionyl chloride (8.7 ml, 0.12 mole) is added dropwise, and after the addition, the mixture heated for a further 3 hours. A further 5.8 ml (0.08 mole) thionyl chloride is added and heating continued for a further 2.5 hours. The mixture is cooled down, filtered and the solvent removed in vacuo leaving the product as a pale yellow oil which can be crystallized from etherhexane, melting point 48°–51° C.

Other solvents such as chloroform, benzene, toluene, ethylene dichloride, and the like, can be used in place of methylene chloride. Other reagents such as acetic anhydride and acetyl chloride may be used in place of thionyl chloride, and the temperature employed can vary from about 10°–130° C.

The following Table V lists the phthalimidonitriles prepared by essentially the above procedure.

TABLE V

| X | $R_1$ | $R_2$ | Melting Point °C |
|---|---|---|---|
| H | —CH$_3$ | —CH(C$_2$H$_5$)$_2$ | oil |
| H | —CH$_3$ | —CH(CH$_3$)(C$_2$H$_5$) | oil |
| H | —CH—CH$_2$—CH$_2$—CH$_2$—CH$_2$—<br>\|<br>CH$_3$ | | 86-87.5 |
| H | —CH$_3$ | —CH(C$_2$H$_5$)$_2$ | — |

Step 4. Preparation of the Phthalimidocarboxamides.

The following is a typical procedure:

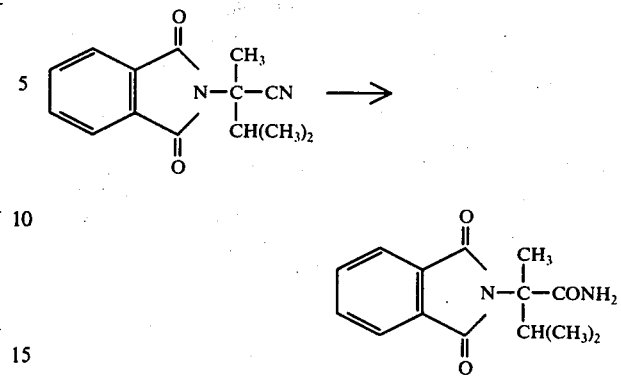

To 404 ml of 85% sulfuric acid is added, with stirring and cooling to maintain a temperature of 14°–16° C, 242.3 g α-isopropyl-α-methyl-1,3-dioxo-2-isoindolineacetonitrile in 67 ml methylene chloride. After the addition (2 hours), the cooling bath is removed and the mixture stirred a further 2 hours at room temperature. The reaction mixture is then poured into a stirred mixture of 2 l water and 300 ml toluene. After 1 hour, the crystalline solid is removed by filtration, washed thoroughly with water, suspended in aqueous sodium bicarbonate solution and again filtered. After washing the solid with water, the product, α-isopropyl-α-methyl-1,3-dioxo-2-isoindolineacetamide, is air-dried and has melting point 165°–166.5° C.

The concentration of the sulfuric acid may be varied from about 70–100%, and the temperature from about 0°–50° C. Co-solvents such as chloroform, ethylenedichloride, may also be used.

The compounds listed in Table VI below are prepared using essentially the same method described above.

TABLE VI

| X | $R_1$ | $R_2$ | Melting Point °C |
|---|---|---|---|
| H | —CH$_3$ | —CH(CH$_3$)(C$_2$H$_5$) | 129–135 |
| H | —CH—CH$_2$—CH$_2$—CH$_2$—CH$_2$—<br>\|<br>CH$_3$ | | 204.5–205.5 |
| H | —CH$_3$ | —CH(C$_2$H$_5$)$_2$ | 122.5–124.5 |

EXAMPLE 5

Alternate Three-Step Synthesis for the Preparation of Phthalimidocarboxamides Essential for the Preparation of Formula I, Imidazoisoindolediones.

Step 1. Preparation of the Phthalimidocarboxylic Acids.

The following procedure is typical:

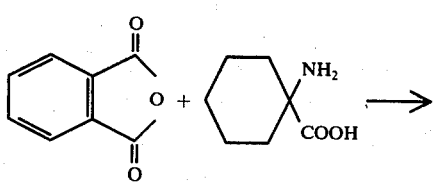

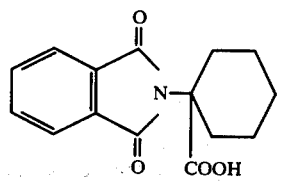

A mixture of 444 g (3 mole) phthalic anhydride, 430 g (3.0 mole) 1-aminocyclohexanecarboxylic acid and 39 ml triethylamine in 4.5 l toluene is heated under reflux with stirring under a Dean-Stark water separator for 21 hours. During this time, 54 ml water is collected. The mixture is slowly cooled to room temperature during which time the product crystallizes from the solution. The product, 1-phthalimidocyclohexanecarboxylic acid, 576.4 g, melting point 176°–178° C, is collected, washed with toluene and airdried.

Other solvents such as acetic acid, benzene, dimethylformamide, xylenes and the like, as well as direct fusion of the two reactants can be used to effect this reaction at temperatures from about 50°–250° C.

The following compounds listed in Table VII are prepared by essentially the same procedure using the appropriate amino acid and phthalic anhydride.

TABLE VII

| X | $R_1$ | $R_2$ | Melting Point °C |
|---|---|---|---|
| H | —CH$_3$ | —CH$_2$CH(CH$_3$)$_2$ | 133–135 |
| 3-Cl | | (CH$_2$)$_5$ | 193–194 |

Step 2. Preparation of the Phthalimidocarbonyl Chlorides.

The following procedure is typical:

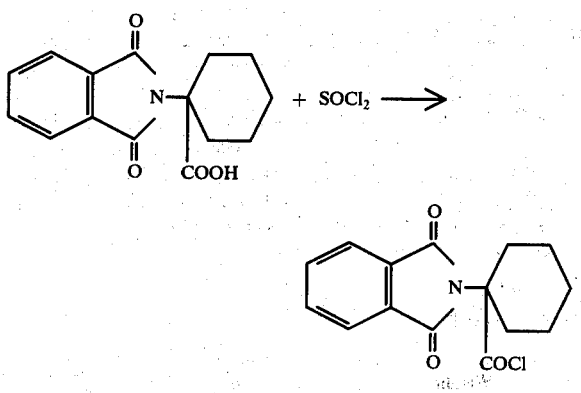

A stirred slurry of 300 g (1.1 mole) 1-phthalimidocyclohexanecarboxylic acid in 2.5 l benzene containing 96 ml (157 g, 1.32 mole) thionyl chloride is heated under reflux for 3.25 hours. The solution is then cooled, filtered and the solvent removed in vacuo to leave the 1-phthalimidocyclohexanecarbonyl chloride as an oil, characterized only by its infrared spectrum and used directly for Step 4, described below.

Other solvents such as chloroform, methylene chloride, dichloroethylene, toluene, xylene, and the like, may be used for this reaction at temperatures from about 20°–100° C. Also, other halogenating agents such as thionyl bromide, phosphorus oxychloride may be employed to prepare the reactive acyl halide.

The following compounds, listed in Table VIII and characterized only by their infrared spectra, are prepared by essentially the same procedure.

TABLE VIII

| X | $R_1$ | $R_2$ |
|---|---|---|
| H | —CH$_3$ | —CH$_2$CH(CH$_3$)$_2$ |
| 3-Cl | | (CH$_2$)$_5$ |

Step 3. Preparation of the Phthalimidocarboxamides.

The following is a typical procedure:

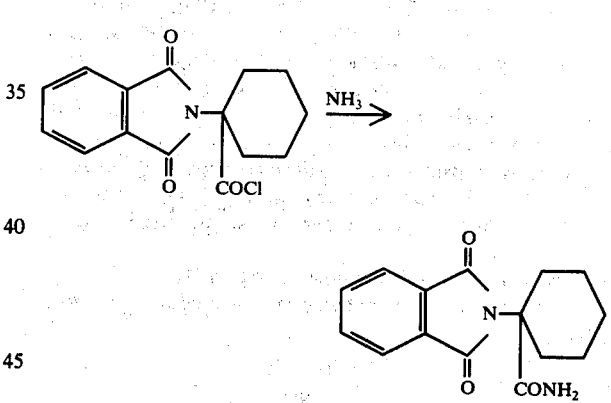

The crude 1-phthalimidocyclohexanecarbonyl chloride prepared above in Step 3 is dissolved in 3.5 l tetrahydrofuran, and the solution cooled to 5 C. Ammonia is then bubbled into the solution with stirring until infrared analysis of the liquid phase indicates that all the acid chloride is converted to the amide. The reaction mixture is then poured into 8 l of water with stirring, the product removed by filtration, washed with water and air-dried to give 259.1 g of 1-phthalimidocyclohexanecarboxamide, melting point 224°–226° C.

Other solvents such as dioxan, toluene and ether may be used instead of tetrahydrofuran at temperatures preferably between 0°–25° C. When water-immiscible solvents are used, the organic phase must be separated, dried and the solvent removed in vacuo and the product crystallized from an appropriate solvent.

The compounds listed in the following Table IX are prepared by essentially the same procedure.

TABLE IX

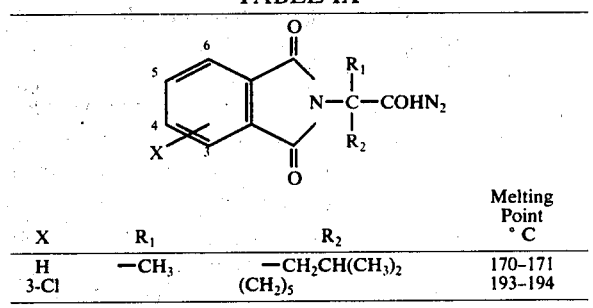

| X | R₁ | R₂ | Melting Point ° C |
|---|---|---|---|
| H | —CH₃ | —CH₂CH(CH₃)₂ | 170–171 |
| 3-Cl | | (CH₂)₅ | 193–194 |

EXAMPLE 6

Preparation of Phthalamic Acid Esters which are Intermediates for the Preparation of Formula I, Imidazoisoindolediones.

Step 1. Preparation of α-Aminocarboxamides.
The following procedure is typical:

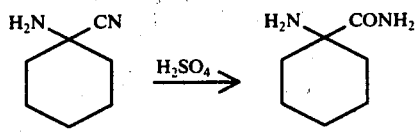

To 20 g concentrated sulfuric acid at 5° C is added with stirring 10 g of 1-aminocyclohexanecarbonitrile. After the addition, the mixture is heated with stirring at 100° C for 1 hour. The hot solution is then poured onto ice, the solution made strongly basic with 50% aqueous sodium hydroxide solution, and extracted three times with chloroform. The extract is washed with water, saturated NaHCO₃ solution, dried, and the solvent removed in vacuo to leave the product, 1-aminocyclohexanecarboxamide, as a crystalline residue, melting point 99°–102° . This can be recrystallized from either benzene or ether or give a pure product, melting point 101°–102° C.

The α-aminocarboxamides listed in Table X below were prepared by essentially the procedure described above.

TABLE X

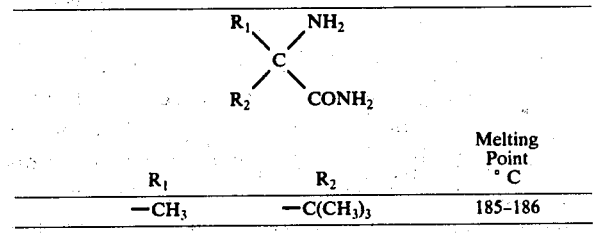

| R₁ | R₂ | Melting Point ° C |
|---|---|---|
| —CH₃ | —C(CH₃)₃ | 185–186 |

Step 2. Preparation of the Phthalamic Acid Esters.
The following is a typical procedure:

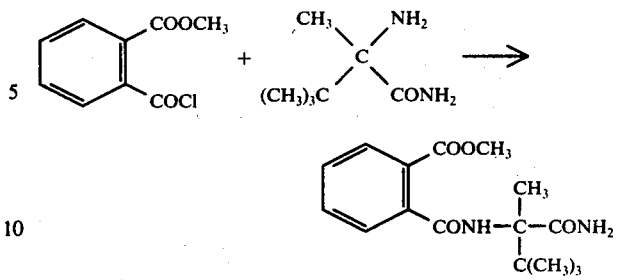

To a stirred suspension of 16.3 g (0.113 mole) of 2-amino-2,3,3-trimethylbutyramide in 226 ml dry tetrahydrofuran containing 16.4 ml dry triethylamine at 5° C is added dropwise a solution containing 22.4 g (0.133 mole) of 2-carbomethoxybenzoyl chloride [Rec. Trav. Chem. 92, 824 (1973)] dissolved in 56 ml dry tetrahydrofuran. After the addition, the mixture is stirred at room temperature for 2 hours and then poured into 400 ml ice cold water. The product was extracted into ethyl acetate, the extract dried over sodium sulfate, the drying agent removed by filtration, and the solvent removed in vacuo. The residual oil crystallizes and the product, methyl N-(1-carbamoyl-1,2,2-trimethylpropyl)-phthalamate, recrystallized from acetone-hexane, melting point 146°–147° C.

Other solvents such as ether, dioxane, benzene, toluene, methylene chloride, chloroform, and the like, may be used instead of tetrahydrofuran at temperatures from about 0°–50° C, but preferably at 5°–25° C.

EXAMPLE 7

Control of Axillary Tobacco Buds.

Seedling tobacco plants are transplanted into six-inch plastic pots containing a greenhouse soil mix (loam soil:sand:muck, 1:1:1). The plants are grown in the greenhouse for 8 to 10 weeks and then topped just above the eleventh node. The active ingredients are applied as foliar sprays to the entire plant, immediately after topping. Each spray solution is prepared by dissolving the desired amount of active ingredient in an acetone-water mixture containing 0.5% TWEEN 20, polyoxyethylene sorbitan monolaurate (Atlas Powder Company). The plant to be sprayed is placed on a turntable and 40 ml of the spray solution applied to the plant from three directed nozzles. The concentration of active ingredient in the spray solution is 200 ppm and 1000 ppm. After spraying, the plants are placed at random on a greenhouse bench and watered normally for a period of 2 weeks. At the termination of each test, the suckers are removed from all nodes, weighed and the results expressed as percent inhibition compared with the fresh weight of suckers from untreated controls. The results achieved are set forth in Table XI below. Maleic hydrazide, a commercial bud growth regulant is included for comparison.

TABLE XI

Tobacco Sucker Inhibition

| Compound | Fresh Weight of Suckers | | | | Average Sucker Weight | | % Sucker Inhibition | |
|---|---|---|---|---|---|---|---|---|
| | Replicate I | | Replicate II | | | | | |
| | 200 ppm | 1000 ppm | 200 ppm | 1000 ppm | 200 ppm | 1000 ppm | 200 ppm | 1000 ppm |
| Untreated Controls | 13.0 15.4 | | 39.4 28.3 | | 25.8* | — | — | |

TABLE XI-continued

Tobacco Sucker Inhibition

| Compound | Fresh Weight of Suckers | | | | Average Sucker Weight | | % Sucker Inhibition | |
|---|---|---|---|---|---|---|---|---|
| | Replicate I | | Replicate II | | | | | |
| | 200 ppm | 1000 ppm | 200 ppm | 1000 ppm | 200 ppm | 1000 ppm | 200 ppm | 1000 ppm |
| Maleic Hydrazide | 21.2 | | 33.7 | | | | | |
| | 20.4 | 6.3 | 22.0 | 2.2 | 21.2 | 4.2 | 18 | 84 |
| | 2.3 | 0 | 5.6 | 0 | 2.8 | 0 | 89 | 100 |

*Average Sucker Weight 6 Replications.

EXAMPLE 8

Plant Growth Regulating Effect of Test Compounds Applied to the Foliage of Plants and to Soil Containing Seeds of Said Plants.

To evaluate test compounds as plant growth regulating agents, said compounds are dissolved or dispersed in 50/50 aqueous acetone mixtures and applied to the foliage of seedling plants and to seeded pots of test plant species.

The plant species use in these tests are as follows:

| Plant | Variety |
|---|---|
| Fescue | Kentucky-31 |
| Sorghum | W-55 |
| Rice | Nato |
| Wheat | Bonanza |
| Barley | Larker |
| Corn | XL-45 |
| Soybean | Adelphia |
| Cotton | Stoneville |
| Cucumber | Marketer |
| Snapbean | Sprite |
| Peanut | NC-2 |
| Sugarbeet | Monogerm |

Treatment consisted of spraying the test compound in acetone:water (1:1) at the rate of 86 gallons per acre with a moving nozzle on a stationary track. The spray nozzle moved at a constant speed over the test species.

In soil treatment tests, containers are filled to within one inch of the top with greenhouse potting soil, tamped, seeds of test plant species placed on top of the soil, sprayed, then covered with additional potting soil. The pots are watered immediately after treatment and benched at random in the greenhouse. Normal watering and fertilizing practices are followed. Minimum day and night temperatures of 65° F are maintained during cooler portions of the year. Normal daily temperature fluctuations occur during the summer season.

Foliage tests are conducted in the same manner described previously in the soil tests. However, the same plant species employed in this test are well established seedlings approximately 2 to 3 inches in height. Plants are watered prior to treatment and are sprayed to provide the same rate of 0.25 and 4 pounds per acre or 0.28 and 4.48 kg per hectare of test compound.

Data Recording

Initial observations are made at 3 to 5 days after treatment for early germination of test species. Morphological changes from the norm are noted during the test period. Final observations are made four weeks after treatment. At this time, measurements of the height of plants are made. From these measurements, increases or decreases as compared to control plants can be noted. Data obtained for both treatments (I = foliar and Ii = soil) are reported in Table XII and XIII below.

Rating Scale:
1 — No effect
2 — Poor activity
3 — Fair activity
4 — Good activity
5 — Excellent activity
6. — Toxic
- — Inhibition or dwarfing
D — Dead

TABLE XII

Observed Plant Growth Enhancement or Dwarfing

| Compound | Rate kg per Hectare | FE I | FE II | SOR I | SOR II | RI I | RI II | WH I | WH II | BA I | BA II | COR I | COR II | SOY I | SOY II | COT I | COT II | CU I | CU II | SN I | SN II | PN I | PN II | SB I | SB II |
|---|---|---|---|---|---|---|---|---|---|---|---|---|---|---|---|---|---|---|---|---|---|---|---|---|---|
| 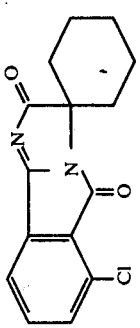 Cl | 0.28<br>1.12 | 1<br>3 | 1<br>3 | 1<br>3 | 1<br>1 | 1<br>1 | 1<br>1 | 1<br>2 | 1<br>1 | 1<br>2 | 1<br>2 | 1<br>2 | 2<br>2 | 3<br>5 | 4<br>4 | 1<br>1 | 1<br>1 | 1<br>2 | 1<br>3 | 1<br>—6 | 1<br>3 | 1<br>1 | 1<br>1 | 1<br>1 | 1<br>2 |
| 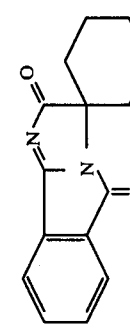 Cl | 0.28<br>1.12 | 3<br>4 | 3<br>5 | 3<br>4 | 3<br>1 | 3<br>4 | 1<br>1 | 3<br>4 | 2<br>3 | 3<br>4 | 2<br>3 | 3<br>4 | 3<br>1 | 4<br>5 | 2<br>3 | 2<br>3 | 1<br>2 | 3<br>4 | 2<br>2 | 3<br>4 | 2<br>4 | 1<br>2 | 1<br>1 | 2<br>3 | 2<br>2 |
| 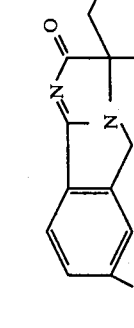 | 1.12<br>4.48 | —5<br>—5 | —1<br>—3 | —3<br>—4 | —1<br>—2 | —1<br>—6 | —6<br>—6 | —6<br>—5 | —2<br>—5 | —5<br>—5 | —1<br>—3 | —1<br>—6 | —1<br>—1 | —6<br>—6 | —1<br>—6 | —1<br>—1 | —1<br>—1 | —6<br>—6 | —1<br>—2 | —6<br>—6 | —1<br>—6 | —1<br>—1 | —1<br>—1 | —6<br>—6 | —1<br>—5 |
|  | 1.12<br>4.48 | —1<br>—4 | —2<br>—3 | —1<br>—6 | —1<br>—6 | —1<br>—1 | —1<br>—6 | —1<br>—5 | —2<br>—5 | —1<br>—5 | —1<br>—3 | —1<br>—6 | —1<br>—3 | —1<br>—5 | —1<br>—6 | —1<br>—1 | —1<br>—1 | —6<br>—6 | —1<br>—6 | —1<br>—5 | —1<br>—2 | —1<br>—1 | —1<br>—1 | —1<br>—2 | —1<br>—2 |
|  CH₃ and | 1.12<br>4.48 | —4<br>—5 | —3<br>—5 | —1<br>—4 | —1<br>—6 | —1<br>—1 | —6<br>—6 | —1<br>—2 | —1<br>—3 | —1<br>—5 | —1<br>—3 | —1<br>—4 | —1<br>—3 | —2<br>—4 | —1<br>—2 | —1<br>—1 | —1<br>—1 | —1<br>—6 | —1<br>—6 | —2<br>—4 | —1<br>—2 | —1<br>—1 | —1<br>—1 | —1<br>—6 | —1<br>—5 |

TABLE XII-continued

Observed Plant Growth Enhancement or Dwarfing

| Compound | Rate kg per Hectare | FE I | FE II | SOR I | SOR II | RI I | RI II | WH I | WH II | BA I | BA II | COR I | COR II | SOY I | SOY II | COT I | COT II | CU I | CU II | SN I | SN II | PN I | PN II | SB I | SB II |
|---|---|---|---|---|---|---|---|---|---|---|---|---|---|---|---|---|---|---|---|---|---|---|---|---|---|
| ![structure with CH₃] | 1.12 | −1 | −1 | −1 | −1 | −1 | −1 | −1 | −1 | −1 | −1 | −1 | −1 | −1 | −1 | −1 | −1 | −1 | −1 | −1 | −1 | −1 | −1 | −1 | −1 |
|  | 4.48 | −1 | −2 | −1 | −1 | −1 | −1 | −1 | −5 | −1 | −4 | −1 | −1 | −2 | −2 | −1 | −3 | −1 | −4 | −1 | −3 | −1 | −1 | −1 | −2 |
| ![structure with CH₃S] and ![structure with CH₃S] | 0.28 | −5 | −5 | −6 | −6 | −1 | −6 | −4 | −5 | −6 | −6 | −6 | −6 | −1 | −5 | −1 | −6 | −6 | −6 | −3 | −3 | −3 | −6 | −5 | −6 |
|  | 1.12 | −5 | −6 | −6 | −6 | −6 | −6 | −5 | −5 | −6 | −6 | −6 | −6 | −6 | −5 | −6 | −6 | −6 | −6 | −5 | −5 | −5 | −6 | −6 | −6 |
|  | 4.48 | −6 | −6 | −6 | −6 | −6 | 0 | −6 | −6 | −6 | −6 | −6 | −6 | −6 | −6 | −6 | −6 | −6 | −6 | −6 | −6 | −6 | −6 | −6 | −6 |
| ![structure with CH(CH₃)₂ and CH₃] |  |  |  |  |  |  |  |  |  |  |  |  |  |  |  |  |  |  |  |  |  |  |  |  |  |

I = Foliar Treatment
II = Soil Treatment
FE = Fescue
SOR = Sorghum
RI = Rice
WH = Wheat
BA = Barley
COR = Corn
SOY = Soybean
COT = Cotton
CU = Cucumber
SN = Snapbean
PN = Peanut
SB = Sugar beet

TABLE XIII
Measurement of Plant Growth Enhancement or Dwarfing
| Compound | Rate kg per Hectare | FE I | FE II | SOR I | SOR II | RI I | RI II | WH I | WH II | BA I | BA II | COR I | COR II | SOY I | SOY II | COT I | COT II | CU I | CU II | SN I | SN II | PN I | PN II | SB I | SB II |
|---|---|---|---|---|---|---|---|---|---|---|---|---|---|---|---|---|---|---|---|---|---|---|---|---|---|
| 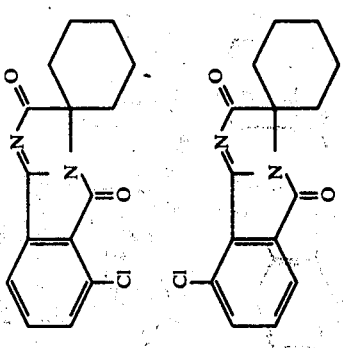 | 0.28 / 1.12 | 38 / 28 | 40 / 28 | 68 / 78 | 66 / 63 | 24 / 27 | 33 / 37 | 31 / 28 | 34 / 34 | 48 / 44 | 44 / 47 | 87 / 90 | 71 / 68 | 53 / 68 | 38 / 38 | 40 / 43 | 39 / 36 | 38 / 33 | 43 / 51 | 31 / 34 | 34 / 42 | 36 / 37 | 27 / 33 | D / 19 | 16 / 16 |
| 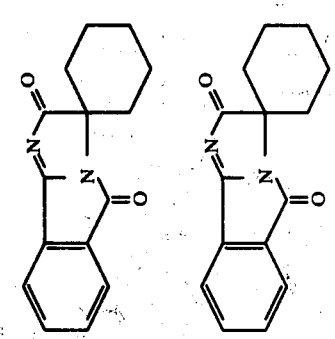 | 0.28 / 1.12 | 25 / 33 | 32 / 31 | 71 / 73 | 58 / 60 | 31 / 28 | 40 / 42 | 25 / 26 | 36 / 35 | 32 / 41 | 45 / 45 | 90 / 82 | 71 / 62 | 57 / 55 | 37 / 36 | 33 / 37 | 32 / 33 | 62 / 43 | 43 / 40 | 36 / 37 | 35 / 32 | 41 / 28 | 34 / 27 | 10 / 16 | 15 / 16 |
| 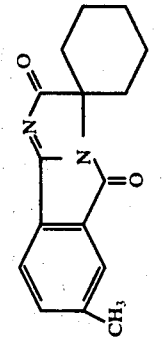 | 1.12 / 4.48 | 21 / 23 | 29 / 33 | 50 / 32 | 61 / 60 | 22 / 18 | 32 / 21 | 18 / 17 | 36 / 35 | 28 / 16 | 42 / 47 | 80 / 80 | 60 / 61 | 26 / 13 | 40 / 38 | 38 / 36 | 32 / 31 | 32 / 18 | 39 / 38 | 25 / 13 | 30 / 24 | 36 / 37 | 21 / 25 | D / D | 14 / 16 |
| 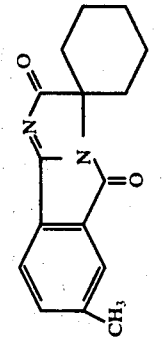 | 4.48 | 21 | 25 | 30 | 60 | 16 | 21 | 20 | 25 | 29 | 48 | 79 | 60 | 26 | 31 | 39 | 28 | 20 | 31 | 21 | 17 | 33 | 29 | D | 7 |
|  | 4.48 | 15 | 20 | 61 | 30 | 23 | 5 | 22 | 30 | 36 | 24 | 73 | 72 | 38 | 32 | 34 | 27 | 18 | 28 | 26 | 23 | 31 | 25 | D | 5 |
and

TABLE XIII-continued
Measurement of Plant Growth Enhancement or Dwarfing

| Compound | Rate kg per Hectare | FE | | SOR | | RI | | WH | | BA | | COR | | SOY | | COT | | CU | | SN | | PN | | SB | |
|---|---|---|---|---|---|---|---|---|---|---|---|---|---|---|---|---|---|---|---|---|---|---|---|---|---|
| | | I | II | I | II | I | II | I | II | I | II | I | II | I | II | I | II | I | II | I | II | I | II | I | II |
| (structure: CH₃-phenyl cyclohexyl imide) | 0.28 | 22 | 26 | 24 | 59 | 23 | 19 | 28 | 27 | 24 | 42 | 28 | 54 | 22 | 28 | 34 | 30 | 15 | 11 | 10 | 28 | 24 | D | 5 |
| | 1.12 | 15 | 3 | D | 3 | 13 | 22 | D | 20 | D | 24 | D | 5 | 18 | 14 | 41 | 22 | 14 | 4 | 0 | 7 | 26 | 20 | D | D |
| (structure: CH(CH₃)₂, CH₃ imide) | 4.48 | 23 | 25 | 69 | 57 | 28 | 25 | 26 | 24 | 35 | | 96 | 60 | 53 | 26 | 38 | 18 | 42 | 27 | 29 | 25 | 34 | 22 | 20 | 16 |
| and (CH₃S-phenyl cyclohexyl imide) | — | | | | | | | | | | | | | | | | | | | | | | | | |
| (CH₃S-phenyl cyclohexyl imide) | — | | | | | | | | | | | | | | | | | | | | | | | | |
| Untreated Controls | — | 28 | 27 | 72 | 63 | 24 | 31 | 27 | 33 | 41 | 42 | 92 | 68 | 56 | 33 | 40 | 28 | 52 | 26 | 30 | 25 | 41 | 28 | 14 | 15 |
| Untreated Controls | — | 28 | 24 | 69 | 62 | 31 | 26 | 21 | 36 | 43 | 48 | 86 | 69 | 46 | 36 | 36 | 32 | 61 | 31 | 21 | 28 | 30 | 28 | 13 | 17 |
| Untreated Controls | — | 23 | 28 | 75 | 60 | 32 | 34 | 24 | 36 | 42 | 45 | 74 | 65 | 42 | 30 | 28 | 27 | 37 | 27 | 28 | 26 | 30 | 27 | 16 | 17 |
| Untreated controls | — | 33 | 21 | 68 | 58 | 35 | 27 | 29 | 33 | 40 | 51 | 69 | 64 | 50 | 37 | 34 | 34 | 50 | 36 | 23 | 21 | 32 | 28 | 10 | 17 |
| Untreated Controls | — | 34 | 24 | 65 | 60 | 28 | 27 | 29 | 33 | 49 | 43 | 90 | 66 | 50 | 35 | 36 | 32 | 50 | 36 | 21 | 28 | 38 | 33 | 11 | 14 |

TABLE XIII-continued

Measurement of Plant Growth Enhancement or Dwarfing

| Compound | Rate kg per Hectare | Plant Weight in Grams | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | FE | | SOR | | RI | | WH | | BA | | COR | | SOY | | COT | | CU | | SN | | PN | | SB | | | | | | | |
| | | I | II | I | II | I | II | I | II | I | II | I | II | I | II | I | II | I | II | I | II | I | II | I | II | | | | | | |
| Average of Untreated Controls | — | 29 | 25 | 70 | 61 | 30 | 29 | 26 | 34 | 43 | 46 | 82 | 66 | 49 | 34 | 35 | 31 | 50 | 31 | 25 | 26 | 34 | 29 | 13 | 16 | | | | | | |

I = Foliar Treatment  
II = Soil Treatment  
FE = Fescue  
SOR = Sorghum  
RI = Rice  
WH = Wheat  
BA = Barley  
COR = Corn  
SOY = Soybean  
COT = Cotton  
CU = Cucumber  
SN = Snapbean  
PN = Peanut  
SB = Sugar beet

EXAMPLE 9

Evaluation of Test Compounds as Plant Growth Regulating Agents.

In these tests, containers are prepared by putting 100 ml of soil (soil type described previously) in each 2¾ inch square plastic pot as a base, then three Amsoy soybean seeds are placed on this base and are covered with soil (⅜ to ½ inch). Seeds of Kentucky 31 Fescue are separately mixed with soil and 50 ml of the soil-seed mix are added to the pot to provide each pot with approximately 625 fescue seeds.

To prepare the test compounds, 20 mg of the compound is placed into a two-ounce, wide-mouth glass bottle and dissolved or dispersed in a 50/50 acetone/water mixture sufficient to prepare a 1000 ppm solution of suspension.

An addition of 5 ml of the 1000 ppm solution in each cup is equivalent to 10 lbs/acre or 11.2 kg/hectare.

Just prior to the application of the compounds, the test pots are tamped to level the soil and are lightly watered to prevent formation of air pockets and channelling routes during application which would prevent even distribution of the test compound in the soil with a pipettor. Three replications are used for each compound.

Each test includes 5 ml of 1:1 acetone:water controls, 5 ml water controls as a standard for comparison of activity from test to test. The treated plants are benched in the greenhouse and normal watering practices are followed. Minimum day and night temperatures of 65° F are maintained during cooler portions of the year. Normal daily temperature fluctuations occur during the summer season. Data obtained are reported below in Table XIV.

Data Recording

Initial observations are made at 3 to 5 days after treatment for early germination of both test species. Physiological or morphological changes from the norm are noted during the test period. Final observations are made at two to three weeks after treatment (dependent on time of year). At this time, measurements of the height of plants of both species are made. From these measurements, percent increases or decreases as compared to control plants, are calculated.

From the data reported below, it can be seen that all compounds tested increased the height of soybean plants; that with the exception of 7' (and 8')-methyl-spiro{cyclohexane-1,3'-(3H)imidazo[2,1-a]isoinodole}-2',5'-dione; 9'-chloro-1',9'b-dihydro-spiro{cyclohexane-1,3'-(3H)imidazo-[2,1-a]isoindole}-2',5'-dione; and 9(or 6)-chloro-3-isobutyl-3-methyl-5H-imidazo[2,1-a]isoindole-2(3H),5-dione, all showed an increase in soybean plant weight; that 9'-chloro-spiro-{cyclohexane-1,3'-(3H)imidazo[2,1-a]isoindole}-2',5'-dione; 9(or 6)-chloro-3-isobutyl-3-methyl-5H-imidazo[2,1-a]isoindole-2(3H),5-dione and 9'-chloro-1',9'b-dihydro-spiro{cyclohexane-1,3'-(3H)imidazo[2,1-a]isoindole}-2',5'-dione, caused a pronounced increase in fescue weight and a weight increase, and that the 7'(and 8')-methyl-spiro{cyclohexane-1,3+-(3H)imidazo-[2,1-a]isoindole}-2',5'-dione and 3-isobutyl-3-methyl-5H-imidazo[2,1-a]isoindole-2(3H),5-dione caused pronounced dwarfing of the fescue.

TABLE XIV

Plant Growth Regulating Effect of Test Compounds on Soybeans and Fescue

| Compound | Soybean Height (cm) | Soybean Weight (g) | Fescue Height (cm) | Fescue Weight (g) |
|---|---|---|---|---|
| Untreated Controls Average of Ten Replicates | 14.5 | 6.31 | 14.0 | 4.47 |
| 9'-Chloro-spiro{cyclohexane-1,3'-(3H)-imidazo[2,1-a]iso-indole}-2',5'-dione | 25.0 | 7.2 | 24.0 | 6.1 |
| | 30.0 | 6.3 | 24.0 | 5.6 |
| | 23.0 | 7.6 | 26.0 | 5.0 |
| 9'-Chloro-1',9'b-dihydro-spiro{cyclohexane-1,3'-(3H)-imidazo[2,1-a]iso-indole}-2',5'-dione | 16.0 | 5.5 | 22.0 | 4.9 |
| | 17.0 | 6.8 | 22.0 | 5.2 |
| | 15.0 | 6.0 | 24.0 | 4.8 |
| 7'(and 8')-ethyl-spiro{cyclohexane-1,3'-(3H)imidazo-[2,1-a]isoindole}-2',5'-dione | 19.0 | 4.6 | 10.0 | 1.4 |
| | 14.0 | — | 8.0 | 0.9 |
| | 14.0 | — | 9.0 | 1.2 |
| 3-Isobutyl-3-methyl-5H-imidazo[2,1-a]-isoindole-2(3H),5-dione | 16.0 | 6.1 | 12.0 | 3.5 |
| | 14.0 | 7.4 | 10.0 | 5.2 |
| | 16.0 | 6.9 | 14.0 | 3.8 |
| 6'(and 9')-(Methylthio)-spiro{cyclohexane-1,3'-(3H)-imidazo[2,1-a]-isoindole}-2',5'-dione | 15.0 | 6.5 | 14.0 | 3.7 |
| | 18.0 | 6.8 | 12.0 | 2.8 |
| | 16.0 | 7.2 | 14.0 | 2.9 |
| 6'(or 9')-Chloro-spiro{cyclopentane-1,3'-(3H)imidazo-[2,1-a]isoindole}-2',5'-dione | 15.0 | 6.6 | 15.0 | 3.8 |
| | 15.0 | 6.5 | 14.0 | 4.1 |
| | 17.0 | 6.4 | 16.0 | 2.7 |
| 6(or 9)-Chloro-3-isobutyl-3-methyl-5H-imidazo[2,1-a]-isoindole-2(3H),5-dione, (isomer 1) | 15.0 | 6.6 | 16.0 | 4.5 |
| | 18.0 | 7.4 | 17.0 | 3.9 |
| | 14.0 | 6.5 | 19.0 | 3.8 |
| 9(or 6)-Chloro-3-isobutyl-3-methyl-5H-imidazo[2,1-a]-isoindole-2(3H),5-dione, (isomer 2) | 17.0 | 5.5 | 18.0 | 5.4 |
| | 17.0 | 6.3 | 18.0 | 5.9 |
| | 17.0 | 6.2 | 18.0 | 4.9 |

I claim:

1. A method for controlling the relative stem growth of plants comprising treating the plants with a compound of the formula:

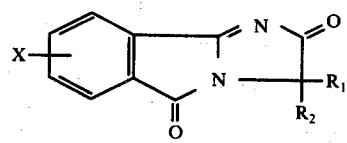

wherein X represents H, CH$_3$, Cl, OCH$_3$, SCH$_3$ or NO$_2$; R$_1$ and R$_2$ each represent alkyl C$_1$–C$_4$, provided that the sum of the carbon atoms in the groups represented by said R$_1$ and R$_2$ is 4 to 7, and when R$_1$ and R$_2$ are taken together with the carbon to which they are attached, they may represent cycloalkyl C$_5$–C$_6$ optionally substituted with CH$_3$; in an amount sufficient to increase or reduce the relative stem length of the treated plant.

2. A method according to claim 1, for increasing the relative stem growth of plants comprising, applying to the foliage of the plant or the soil in which it is growing, from about 0.28 to 11.2 kg/hectare of a compound according to claim 1, wherein X is chloro, R$_1$ and R$_2$ each represent alkyl C$_1$–C$_4$ provided that the sum of the carbon atoms represented thereby is 5 to 7, or when R$_1$ and R$_2$ are taken together with the carbon to which they are attached represent cycloalkyl C$_5$–C$_6$.

3. A method according to claim 2, wherein the compound has the formula:

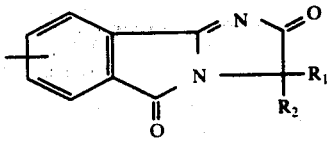

wherein $R_1$ and $R_2$ each represent alkyl $C_1-C_4$, provided that the sum of the carbon atoms represented by $R_1$ and $R_2$ is 5 to 7, or when $R_1$ and $R_2$ are taken together with the carbon to which they are attached they represent cycloalkyl $C_5-C_6$.

4. A method according to claim 2, wherein the compound is 9'-chloro-spiro{cyclohexane-1,3'-(3H)imidazo[2,1-a]-isoindole}-2',5'-dione.

5. A method according to claim 2, wherein the compound is 6-chloro-spiro{cyclohexane-1,3'-(3H)imidazo[2,1-a]isoindole}-2',5'-dione.

6. A method according to claim 2 wherein the compound is 6(or 9)-chloro-3-isobutyl-3-methyl-5H-imidazo]2,1-a]isoindole-2(3H),5-dione.

7. A method according to claim 1, for reducing the relative stem growth of plants comprising, applying to the foilage of the plants or the soil in which it is growing, from about 0.28 to 4.48 kg/hectare of a compound, wherein X is H, $CH_3$, $NO_2$, $OCH_3$ or $SCH_3$, and $R_1$ and $R_2$ are as described in said claim 1.

8. A method according to claim 7, wherein the compound is 3-isopropyl-3-methyl-5H-imidazo[2,1-a]isoindole-2(3H),5-dione.

9. A method according to claim 7, wherein the compound is spiro-{cyclohexane-1,3'-(3H)imidazo[2,1-a]isoindole}-2',5'-dione.

10. A method according to claim 7, wherein the compound is spiro-{cyclopentane-1,3'-(3H)imidazo[2,1-a]isoindole}-2',5'-dione.

11. A method according to claim 1 wherein the compound is 6'-(methylthio)-spiro{cyclohexane-1,3'-(3H)imidazo[2,1-a]-isoindole}-2',5'-dione.

12. A method according to claim 1 wherein the compound is 9'-(methylthio)-spiro{cyclohexane-1,3'-(3H)imidazo[2,1-a]-isoindole}-2',5'-dione.

13. A method according to claim 1 wherein the compound is 6'-chloro-spiro{cyclopentane-1,3'-(3H)imidazo[2,1-a]isoindole}-2',5'-dione.

14. A method according to claim 1 wherein the compound is 9'-chloro-spiro{cyclopentane-1,3'-(3H)imidazo[2,1-a]isoindole}-2',5'-dione.

15. A method according to claim 1 wherein the compound is 3-isobutyl-3-methyl-5H-imidazo[2,1-a]isoindole-2(3H),5-dione.

16. A method according to claim 1 wherein the compound is 7'-methyl-spiro{cyclohexane-1,3'-(3H)imidazo[2,1-a]isoindole}-2',5'-dione.

17. A method according to claim 1 wherein the compound is 8'-methyl-spiro{cyclohexane-1,3'-(3H)-imidazo[2,1-a]isoindole}-2',5'-dione.

18. A method according to claim 1 wherein the compound is (+)-3-isopropyl-3-methyl-5H-imidazo-[2,1-a]isoindole-2(3H),5-dione.

* * * * *